(12) United States Patent
Klewer

(10) Patent No.: US 8,602,642 B2
(45) Date of Patent: Dec. 10, 2013

(54) CONTACT DETECTION DEVICE FOR DETECTING A PHYSICAL CONTACT BETWEEN THE CONTACT DETECTION DEVICE AND AN OBJECT

(75) Inventor: Jasper Klewer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/383,295

(22) PCT Filed: Jul. 7, 2010

(86) PCT No.: PCT/IB2010/053102
§ 371 (c)(1),
(2), (4) Date: Jan. 10, 2012

(87) PCT Pub. No.: WO2011/007294
PCT Pub. Date: Jan. 20, 2011

(65) Prior Publication Data
US 2012/0106592 A1   May 3, 2012

(30) Foreign Application Priority Data

Jul. 14, 2009  (EP) .................................... 09165390

(51) Int. Cl.
*G01N 25/18* (2006.01)
(52) U.S. Cl.
USPC .......................................................... 374/45
(58) Field of Classification Search
None
See application file for complete search history.

(56) References Cited

U.S. PATENT DOCUMENTS

| 3,933,045 | A | * | 1/1976 | Fox et al. ...................... 374/134 |
| 4,052,896 | A | * | 10/1977 | Lee et al. .................... 73/861.29 |
| 4,360,888 | A | * | 11/1982 | Onksen et al. ................ 702/144 |
| 4,399,824 | A | | 8/1983 | Davidson |
| 4,686,998 | A | * | 8/1987 | Robbins ........................ 600/483 |
| 5,632,555 | A | * | 5/1997 | Gregory et al. ............... 374/102 |
| 5,642,105 | A | * | 6/1997 | Duffy et al. .............. 340/870.17 |

(Continued)

FOREIGN PATENT DOCUMENTS

EP   1767913 A1   3/2007

OTHER PUBLICATIONS

Muhammad Imran and Abhijit Bhattacharyya, "Effect of Thin Film Thicknesses and Materials on the Response of RTDs and Microthermocouples", IEEE Sensors Journal, vol. 6, No. 6, Dec. 2006, pp. 1459-1467.*

(Continued)

*Primary Examiner* — Lisa Caputo
*Assistant Examiner* — Nasir U Ahmed

(57) ABSTRACT

The present invention is related to a contact detection device (100) for detecting a contact between the contact detection device (100) and an object (800), a method (400), a diagnostic device and further to a computer program. The invention seeks to improve the reliability of contact sensors. The contact detection device (100) comprises a heater (110) for providing a modulated heat flow (112). A modulated heat signal (122) is generated in dependence of the modulated heat flow (112). A physical contact with an object (800) causes a change in the modulated heat flow (112) that effects the modulated heat signal (122). As the heat flow is modulated, a change in the modulated heat signal (122) is quasi assured. A contact determination unit (130) of the contact detection device (100) derives a contact indication signal (132) indicating at least either the presence or the absence of the physical contact in from the modulated heat (122), preferentially by means of a demodulator (134).

14 Claims, 4 Drawing Sheets

(56) References Cited

U.S. PATENT DOCUMENTS

| | | | |
|---|---|---|---|
| 5,667,300 A * | 9/1997 | Mandelis et al. | 374/43 |
| 5,751,510 A * | 5/1998 | Smith et al. | 360/67 |
| 5,784,004 A * | 7/1998 | Esfahani et al. | 340/854.6 |
| 6,948,360 B2 * | 9/2005 | Lin | 73/146.5 |
| 6,988,026 B2 * | 1/2006 | Breed et al. | 701/31.4 |
| 7,284,904 B2 * | 10/2007 | Tokita et al. | 374/163 |
| 7,314,310 B2 * | 1/2008 | Medero | 374/164 |
| 7,394,395 B2 * | 7/2008 | Sakatani et al. | 340/679 |
| 2005/0265898 A1 * | 12/2005 | Bell et al. | 422/82.01 |
| 2008/0273573 A1 * | 11/2008 | Gerder | 374/164 |

OTHER PUBLICATIONS

J.H. Oum, S.E. Lee, D.-W. Kim and S. Hong, "Non-contact heartbeat and respiration detector using capacitive sensor with Colpitts oscillator", Electronics Letters Jan. 17, 2008 vol. 44 No. 2.*

* cited by examiner

CONTACT DETECTION DEVICE FOR DETECTING A PHYSICAL CONTACT BETWEEN THE CONTACT DETECTION DEVICE AND AN OBJECT

FIELD OF THE INVENTION

The invention relates to a contact detection device, a method of operating a contact detection device and a diagnostic device comprising a contact detection device. The invention further relates to a computer program.

BACKGROUND OF THE INVENTION

European Patent Application EP 1 767 913 A1 discloses a micro sensor for capturing a heat flow. The micro sensor comprises a heat collector wall and a heat sink, wherein the heat sink and the heat collector wall are separated by a planar metal layer with distributed thermal junctions. The heat sink is formed by a porous substrate which guides a heat flux such that a high Seebeck voltage is achieved between two respective thermal junctions. The Seebeck voltage is indicative for a temperature. The disclosed micro sensor shall predominantly be employed for measuring high temperatures, such as 800° C. The micro sensor can also be employed as a contact sensor for detecting a physical contact. A physical contact between the micro sensor and an object causes under certain circumstances a change in voltage if the object exhibits a temperature different from the temperature of the micro sensor. This change in voltage is detectable.

SUMMARY OF THE INVENTION

It is an object of the present invention to provide a contact detection device for detecting a physical contact between the contact detection device and an object, wherein the reliability of the contact detection device is improved.

In a first aspect of the present invention a contact detection device for detecting a physical contact between the contact detection device and an object is presented, wherein the contact detection device comprises:

a heater for providing a modulated heat flow, a heat signal generation unit being adapted to generate a modulated heat signal in dependence of the modulated heat flow, a contact determination unit for determining a contact indication signal indicating at least either the presence or the absence of the physical contact depending on the generated modulated heat signal.

The invention is based on the recognition that the above mentioned prior art contact sensor fails to detect a physical contact between an object and the contact sensor if the object exhibits the same temperature as the contact sensor. If both the contact sensor and the object exhibit the same temperature, the physical contact does not effect a change in heat flow and thus, for instance no change in a measured voltage or a measured temperature. In this case, a physical contact remains undetected.

The invention is based on the further recognition that a contact detection implemented with the above mentioned prior art contact sensor can be corrupted by a change in the ambient temperature. A significant change in ambient temperature may cause a change in the temperature of a part of the contact sensor, thus falsely leading the contact sensor to indicate a contact.

Therefore, the prior art contact sensor lacks in reliability.

Since the heater of the contact detection device of the first aspect of the invention provides a modulated heat flow, at least a temperature sensitive contact surface of the contact detection device assumes a modulated temperature. Therefore, it is ensured that the probability for a change in the amount of the modulated heat flow influencing the modulated heat signal is increased, if the contact detection device physically contacts an object: When contacting the object, for instance the skin of a person, with the contact detection device, either a part of the modulated heat flow flows to the object or an additional heat flow coming from the object amounts to the modulated heat flow provided by the heater.

As the heat signal generation unit generates a modulated heat signal in dependence of the modulated heat flow, the modulated heat signal deviates as well if there is a change in the modulated heat flow. The modulated heat flow that effects the modulated heat signal not only changes if the temperature of the temperature sensitive contact surface of the contact detection device differs from the temperature of the object: The invention is based on the further recognition that the total heat capacity, which is fed by the heater, changes as well, if the contact detection device physically contacts the object. Therefore, a parameter that defines the shape of the modulated heat flow, such as a rate of change of the modulated heat flow and/or an amplitude of the modulated heat flow, changes as well. Therefore, a change of the modulated heat signal that is generated in dependence of the modulated heat flow is quasi assured, if a physical contact between an object and the contact detection device is made.

The contact determination unit determines the contact indication signal indicating the physical contact depending on the modulated heat signal, preferentially by detecting such a deviation of the modulated heat signal. Since it is most unlikely that the temperature of the object changes in the same manner as the modulated heat flow or that the physical contact between the object and the contact detection device does not change the total heat capacity, the presence or the absence of the physical contact between the contact detection device of the first aspect of the invention and the object is quasi assured to be detected. The contact indication signal indicates at least either the presence or the absence of the physical contact. Preferentially, the magnitude of the contact indication signal characterizes further parameters of the contact, such as the quality of contact.

The heater preferentially provides a periodic modulated heat flow. The rate of change of the modulated heat flow is preferentially greater than a common rate of change of an ambient temperature. In a preferred embodiment, the frequency of the modulated heat flow is approximately 1 Hz.

The modulated heat flow provided by the heater can be of any shape, for example a shape of a periodic rectangular signal, of a sinusoidal wave, of a sawtooth signal, of a pulse width modulated signal or of a pseudorandom signal. In particular, the shape of the modulated heat flow provided by the heater can assume a squared characteristic of the aforementioned shapes.

As the heat flow provided by the heater is modulated, the effective heat flow can preferentially be kept low in order to avoid a substantial self-heating of the contact detection device or parts of the contact detection device. This has the further advantage of low power consumption of the contact detection device.

Preferentially, the heat signal generation unit is a thermometer. The thermometer preferentially measures the temperature of the temperature sensitive contact surface of the contact detection device. In this case, the modulated heat signal is a measured temperature.

In a further preferred embodiment, the heat signal generation unit is a thermopile being adapted to generate a modulated electrical signal as the modulated heat signal in dependence of the modulated heat flow.

In yet a further preferred embodiment, the heat signal generation unit is a thermocouple being adapted to generate a modulated electrical signal as the modulated heat signal in dependence of the modulated heat flow.

In another preferred embodiment, the heater of the contact detection device is realized by a thermal resistor connected to a power source.

It shall be understood that within the scope of this description, the wording "thermal resistor" refers to all classes of temperature dependent resistors exhibiting either a positive or negative temperature coefficient, such as a thermistor or a resistance thermometer.

In a preferred embodiment, the thermal resistor connected to the power source is a thermistor. This has the advantage of a very small size and low cost. For example, a thermistor can have an approximate size of $(0.5 \text{ mm})^3$ with negligible costs. Therefore, the contact detection device may be advantageously integrated in other devices. The thermistor may exhibit either a positive or negative temperature coefficient.

Preferentially, the thermal resistor is connected to the temperature sensitive contact surface of the contact detection device.

In this embodiment, the modulated heat signal can be, for example, a measured voltage of the thermal resistor, a measured current flowing through the thermal resistor, a measured power consumption value of the thermal resistor, a measured resistance of thermal resistor or a measured temperature of the thermal resistor. The heat signal generation unit adapted to generate the modulated heat signal is then realized by a respective appropriate measurement device, such as a voltmeter, a current meter, a power meter or a thermometer.

If a self-heating of the thermal resistor is not desired, the effective heat flow can be kept low. This has the advantage of a low power consumption of the contact detection device. In another embodiment, the effective heat flow is kept high, such that the temperature of the thermal resistor is most likely greater than a temperature of an object, whose physical contact to the contact detection device is to be detected. This again increases the reliability of the contact detection device.

It is preferred that the power source of the heater of the contact detection device is adapted to provide a modulated current to the thermal resistor. The modulated current fed to the thermal resistor effects a modulated heat flow. In this embodiment, the modulated heat signal generated by the heat signal generation unit can be a measured voltage of the thermal resistor. This embodiment has the advantage of further reduced size, since the heater can be constructed of a low complex current source directly connected to the thermal resistor.

Alternatively, it is preferred that the power source is adapted to provide a modulated voltage to the thermal resistor. In order to generate certain courses of a modulated heat flow, it can be advantageous to provide a modulated voltage to the thermal resistor instead of a modulated current, as voltage sources are generally less complex to implement. In this embodiment, the modulated heat signal can be a measured current or a measured voltage. In the latter case, a resistor of a substantially constant resistance value is preferentially connected in series to the thermal resistor, such that the voltage of the thermal resistor is unequal to the modulated voltage provided by the voltage source.

In all embodiments of the contact detection device, it is preferred that the contact determination unit comprises a demodulator for demodulating the modulated heat signal to generate a demodulated signal and is adapted to determine the contact indication signal depending on the demodulated signal.

This preferred embodiment of the contact detection device of the first aspect of the invention has the advantage that an influence of the ambient temperature is reduced and the reliability of the contact detection device furthermore improved. The generated demodulated signal contains regained information carrying parameters characterizing the modulated heat flow, such as the amplitude, phase or duty cycle of the modulated heat flow or the frequency of periodic modulated heat flow. As for instance the frequency of the periodic modulated heat flow differs significantly from a rate of change in the ambient temperature, the demodulated signal is substantially independent from the ambient temperature. Therefore, the contact determination unit derives the contact indication signal only from a signal, which depends nearly exclusively on the modulated heat flow and not on the ambient temperature. Therefore, the reliability of the contact detection device is again increased.

Preferentially, the demodulator is adapted to demodulate the modulated heat signal in phase with the modulated heat flow. This preferred embodiment has the advantage that an influence of the ambient temperature is furthermore reduced. Furthermore, this embodiment has the advantage that low complex demodulation functions can be applied. In this embodiment, the contact determination unit is adapted to detect a phase of the modulated heat flow, for example by means of detecting signals in noise, such as in-phase or quadrature synchronous detection, matched filter, frequency domain analysis like Fast Fourier Transformation or Discrete Cosine Transformation or single tone extraction.

In yet a preferred embodiment, the demodulator of the contact determination unit of the contact detection device comprises:
 a first calculation unit being adapted to determine a constant component of the modulated heat signal and to subtract the constant component of the modulated heat signal from the modulated heat signal to generate a first alternating signal,
 a multiplier for multiplying the first alternating signal with a second alternating signal to generate an intermediate signal, wherein the second alternating signal is in phase with the modulated heat flow,
 an average calculation unit for averaging the intermediate signal to generate the demodulated signal.

This preferred embodiment of the demodulator of the contact determination unit of the contact detection device is an exemplary embodiment that ensures that the demodulated signal is substantially independent from a change of the ambient temperature. The modulated heat flow $HF_{DC}(t)$ provided by the heater can for instance be expressed according to equation (1)

$$HF_{DC}(t) = HF_0 + A_1 \cdot \sin(\omega t) + E_1(t), \tag{1}$$

where $HF_0$ is a substantially non-alternating component of the modulated heat flow, $A_1 \cdot \sin(\omega t)$ an alternating component, wherein $A_1$ characterizes the amplitude of the alternating component, $\omega$ the frequency of the alternating component and t the time. $E_1(t)$ characterizes an error term caused by common side effects. For example, if the modulated heat flow is provided by generating a sinusoidal current, this error term is proportional to a squared sine wave.

However, the modulated heat flow provided by the heater can be of any other shape than of a sinusoidal shape, for example a shape of a periodic rectangular signal, of a sawtooth signal, of a pulse width modulated signal or of a pseudorandom signal. In particular, the shape of the modulated heat flow provided by the heater can assume a squared characteristic of the aforementioned shapes.

According to the modulated heat flow of equation (1), the heat signal generation unit generates a modulated heat signal $HS_{DC}(t)$ according to equation (2)

$$HS_{DC}(t)=HS_0(T_{amb},T_{obj})+A_2(C_{obj})\cdot\sin(\omega\cdot t)+E_2(t), \quad (2)$$

where $HS_0$ is a component substantially depending on the ambient temperature $T_{amb}$. If the contact detection device is in physical contact with an object, this component also depends on a temperature $T_{obj}$ of the object. An alternating component of the modulated heat signal is characterized by the term $A_2(C_{obj})\cdot\sin(\omega\cdot t)$. The amplitude $A_2$ of the alternating component depends on the location of the object, whether or not it is in contact with the contact detection device. A physical contact changes the total heat capacity that is fed by the heater. The total heat capacity fed by the heater depends on the heat capacity $C_{obj}$ of the object, if the object is in contact with the contact detection device. That heat capacity $C_{obj}$ of the object also depends on the temperature $T_{obj}$ of the object. As the heat signal generation unit generates the modulated heat signal in dependence of the modulated heat flow, an error term $E_2(t)$ remains part of the modulated heat signal.

The first calculation unit of the demodulator of the contact determination unit is adapted to determine the constant component $HS_{CONST}$ of the modulated heat signal and to subtract the constant component $HS_{CONST}$ from the modulated heat signal $HS_{DC}(t)$ to generate the first alternating signal $HS_{AC}$ according to equation (3)

$$HS_{AC}=HS_{DC}-HS_{CONST} \quad (3)$$

The first alternating signal is therefore substantially independent from the ambient temperature. Preferentially, the constant component of the modulated heat signal is a time averaged component of the modulated heat signal.

The multiplier of the demodulator of the contact determination unit is adapted to multiply the first alternating signal $HS_{AC}$ with a second alternating signal to generate the intermediate signal $HS_{INTER}$, the second alternating signal being in phase with the modulated heat flow; for example according to equation (4)

$$HS_{INTER}=HS_{AC}\cdot\sin(\omega t) \quad (4)$$

Preferentially, the contact determination unit is adapted to determine the second alternating signal by detecting a phase of the modulated heat flow, for example by means of detecting signals in noise, such as in-phase or quadrature synchronous detection, matched filter, frequency domain analysis like Fast Fourier Transformation or Discrete Cosine Transformation or single tone extraction. Alternatively, the second alternating signal can be provided by a phase detection unit of the contact detection device.

The average calculation unit is adapted to average the intermediate signal $HS_{INTER}$ to generate the demodulated signal $HS_{DEMOD}$, preferentially by low-pass filtering the intermediate signal $HS_{INTER}$ according to equation (5)

$$HS_{DEMOD}=LPF(HS_{INTER}) \quad (5)$$

where LPF is a low-pass filtering function. In a preferred embodiment, the average calculation unit is moving average filter. In a further preferred embodiment, the average calculation unit is a butterworth filter. Preferentially the cut-off frequency of both filters is lower than the frequency of the modulated heat flow; for instance its value is approximately equal to the half of the value of the frequency of the periodic modulated heat flow. The generated demodulated signal $HS_{DEMOD}$, is well suitable for determining the contact indication signal, as its value significantly changes if a physical contact between the contact detection device and an object is made. The contact determination unit determines the contact indication signal for example by means of a comparator.

It is preferred that the contact determination unit comprises a comparator for comparing the demodulated signal with a threshold and is adapted to determine the contact indication signal depending on a result of the comparison.

Preferentially, the contact indication signal indicates the presence of the physical contact if a value of the demodulated signal is below the threshold and indicates the absence of the physical contact if a value of the demodulated signal above the threshold. Alternatively it is preferred that the contact indication signal indicates the absence of the physical contact if a value of the demodulated signal is below the threshold and indicates the presence of the physical contact if a value of the demodulated signal above the threshold. Depending on the nature of the modulated heat signal and the definition of the threshold, the first or the second of the above mentioned two possibilities is advantageous.

In this embodiment, the contact determination unit can be adapted such that if the demodulated signal is equal to the threshold, the contact indication signal either indicates presence of the physical contact or absence of the physical contact.

The threshold can be a constant predefined threshold or a changing threshold. Preferentially, the threshold is defined in dependence of the generated modulated heat flow and/or in dependence of a demodulation function of the demodulator of the contact determination unit. This has the advantage that sudden changes of the modulated heat signal can be detected by the contact determination unit. Therefore, the reliability of the contact detection device is furthermore improved.

In yet another preferred embodiment, the contact detection device additionally comprises a controller for controlling the heater such that the modulated heat flow provided by the controlled heater seeks to effect a predefined course of temperature of the thermal resistor.

For example, the controller is a proportional-integral controller. The power source is then realized, for instance, by a proportional-integral controlled current or voltage source. The controller may thus be integrated in the heater are alternatively arranged externally from the heater.

In this embodiment, the heat signal generation unit is preferentially a power consumption measurement unit and adapted to generate a power consumption value of the heater as the modulated heat signal. When contacting an object, the temperature of the thermal resistor deviates. As the controller controls the heater, power consumption of the heater deviates contrary to the deviation of the temperature of the thermal resistor, such the deviation in temperature is reduced. A measured power consumption value is therefore a suitable modulated heat signal to derive the contact indication signal from.

In yet a further advantageous embodiment of the contact detection device, the heater is additionally adapted to provide a constant heat flow.

In this embodiment, the heater of the contact detection device can have primary function of heating. A modulation is added to a constant heat flow such that the substantially constant heat flow is unaltered. Therefore, the primary function of heating is not constricted and the contact detection device remains adapted to detect a physical contact between an object and the heating device.

In a second aspect of the present invention a method of operating a contact detection device is presented, where the method comprises the following steps:
providing a modulated heat flow,
generating a modulated heat signal in dependence of the modulated heat flow,
determining a contact indication signal indicating at least either the presence or the absence of the physical contact depending on the modulated heat signal.

In a third aspect of the present invention a diagnostic device is presented, wherein the diagnostic device comprises the contact detection device of the first aspect of the invention.

This has the advantage that a diagnosis of an object is can be performed after a physical contact between the diagnostic device and the object is ascertained by the contact detection device of the diagnostic device. This advantage is of particular significance in the field of clinical application.

In one embodiment, the diagnostic device of the third aspect of the invention can be a medical device, such as a temperature sensor, in particular a human body temperature sensor. Some temperature sensors only function if they are properly attached to the object whose temperature is to be measured. Therefore, it is advantageous if such a temperature sensor comprises a contact detection device indicating the presence or the absence of a physical contact.

In another embodiment, the diagnostic device is an occupancy detection device for detecting the occupancy of an apparatus, such as a bed or chair.

In a preferred embodiment of the diagnostic device, the contact indication signal provided by the contact detection device is used for operating a switch of the diagnostic device. The switch of the diagnostic device is preferentially employed for activating or deactivating, respectively, further processing means of the diagnostic device.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
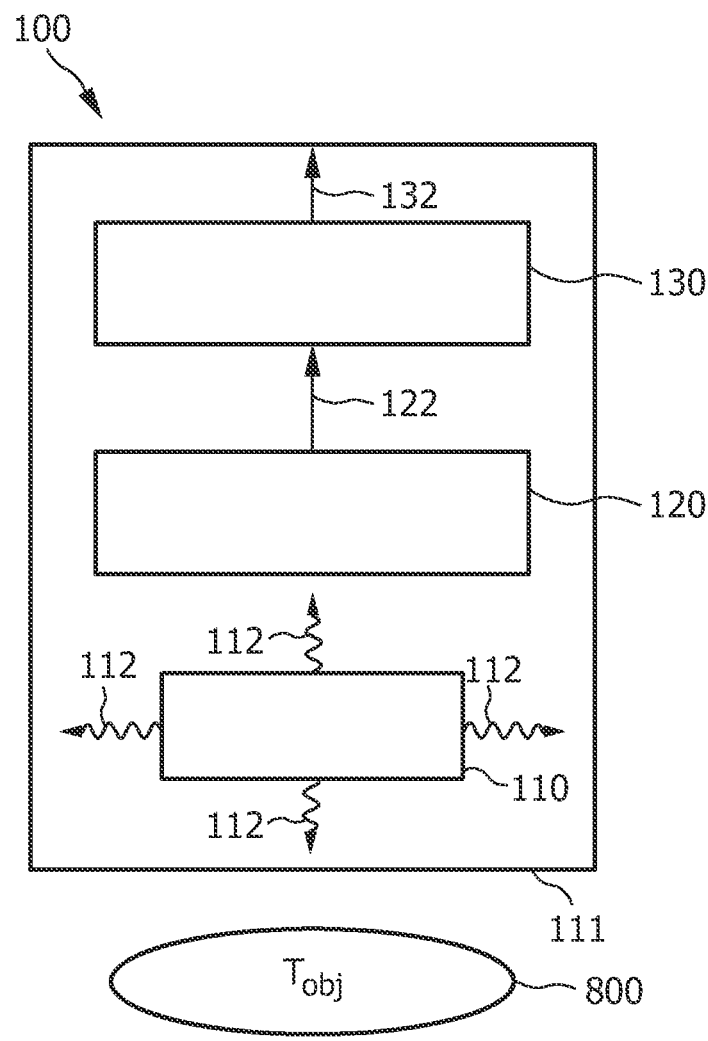
FIG. 1 shows schematically and exemplarily a representation of the contact detection device for detecting a physical contact between the contact detection device and an object in accordance with the first aspect of the invention.

FIG. 1 shows schematically and exemplarily a contact detection device 100 for detecting a physical contact between the contact detection device 100 and an object 800 in accordance with the first aspect of the invention. The contact detection device 100 comprises a heater 110 for providing a modulated heat flow 112. The heater 110 preferentially provides a periodic modulated heat flow 112. The rate of change of the modulated heat flow 112 is preferentially greater than a common rate of change of an ambient temperature. The modulated heat flow 112 provided by the heater 110 can be of any shape, for example a shape of a periodic rectangular signal, of a sinusoidal wave, of a sawtooth signal, of a pulse width modulated signal or of a pseudorandom signal. In particular, the shape of the modulated heat flow 112 provided by the heater 110 can assume a squared characteristic of the aforementioned shapes.

Due to the modulated heat flow 112, at least a temperature sensitive contact surface 111 of the contact detection device 100 assumes a modulated temperature $T_{mod}$. When contacting an object 800 exhibiting a temperature $T_{obj}$, the difference in temperature $\Delta T=|T_{obj}-T_{mod}|$ causes a change in the amount of the modulated heat flow 112, since either heat flows from the contact detection device 100 to the object 800 or from the object 800 to the contact detection device 100. That difference in temperature comprises an alternating and a substantially non-alternating component. The alternating component is caused by the modulated heat flow 112, the substantially non-alternating component characterizes a time averaged temperature difference. As it is most unlikely that the temperature of the object 800 changes in the same manner as the modulated heat flow 112, a change in heat flow is quasi assured if contact is made with the object 800.

For instance, the heater 110 can be realized by a thermal resistor 116, such as a thermistor or a resistance thermometer connected to a power source 114, as explained below in more detail with respect to FIG. 2. In FIG. 1, the housing surface of the contact detection device 100 facing to the object 800 is referenced as the temperature sensitive contact surface 111. However, any part of the housing of the contact detection device 100 may form the temperature sensitive contact surface 111.

The contact detection device 100 further comprises a heat signal generation unit 120 that generates a modulated heat signal 122 in dependence of the modulated heat flow 112. A change in the amount of the modulated heat flow 112 therefore effects a change in the modulated heat signal 122.

The modulated heat flow 112 that effects the modulated heat signal 122 not only changes if the temperature of the temperature sensitive contact surface 111 of the contact detection device 100 differs from the temperature $T_{obj}$ of the object 800: The invention is based on the further recognition that the total heat capacity, which is fed by the heater 110, changes as well, if the contact detection device 100 physically contacts the object 800. Therefore, a parameter that defines the shape of the modulated heat flow 112, such as a phase of the modulated heat flow 112 and/or an amplitude of the modulated heat flow 112, changes as well. Therefore, a change of the modulated heat signal 122 that is generated in dependence of the modulated heat flow 112 is quasi assured, if a physical contact between an object 800 and the contact detection device 100 is made.

The heat signal generation unit 120 can, for instance, be realized by a measurement device that measures a voltage of a thermal resistor 116 of the heater 110. In this case, the modulated heat signal 122 would be a measured voltage.

The heat signal generation unit 120 can also be thermometer that measures a temperature of the temperature sensitive contact surface 111 of the contact detection device 100. In that case, the modulated heat signal 122 is a measured temperature.

In another preferred embodiment, the heat signal generation unit 120 is a thermopile being adapted to generate an modulated electrical signal as the modulated heat signal 122 in dependence of the modulated heat flow 112.

In yet a further preferred embodiment, the heat signal generation 120 unit is a thermocouple being adapted to generate an modulated electrical signal as the modulated heat signal 122 in dependence of the modulated heat flow 112.

Ultimately, the contact detection device 100 comprises a contact determination unit 130 for determining a contact indication signal 132 indicating at least either the presence or the absence of the physical contact depending on the generated modulated heat signal 122, preferentially by detecting a deviation in the modulated heat signal 122.

Since it is most unlikely that the temperature of an object 800 changes in the same manner as the modulated heat flow 112, that deviation in the modulated heat signal 122 is quasi assured. Furthermore, it is most unlikely that the physical contact does not effect a change in the total heat capacity that is fed by the heater 110. That change in the total heat capacity also effects a change in the modulated heat signal. Therefore a detection of the presence or the absence of the physical contact between the contact detection device 100 and the object 800 is quasi assured. Therefore, the reliability of the contact detection device 100 is increased.

Figure 2:
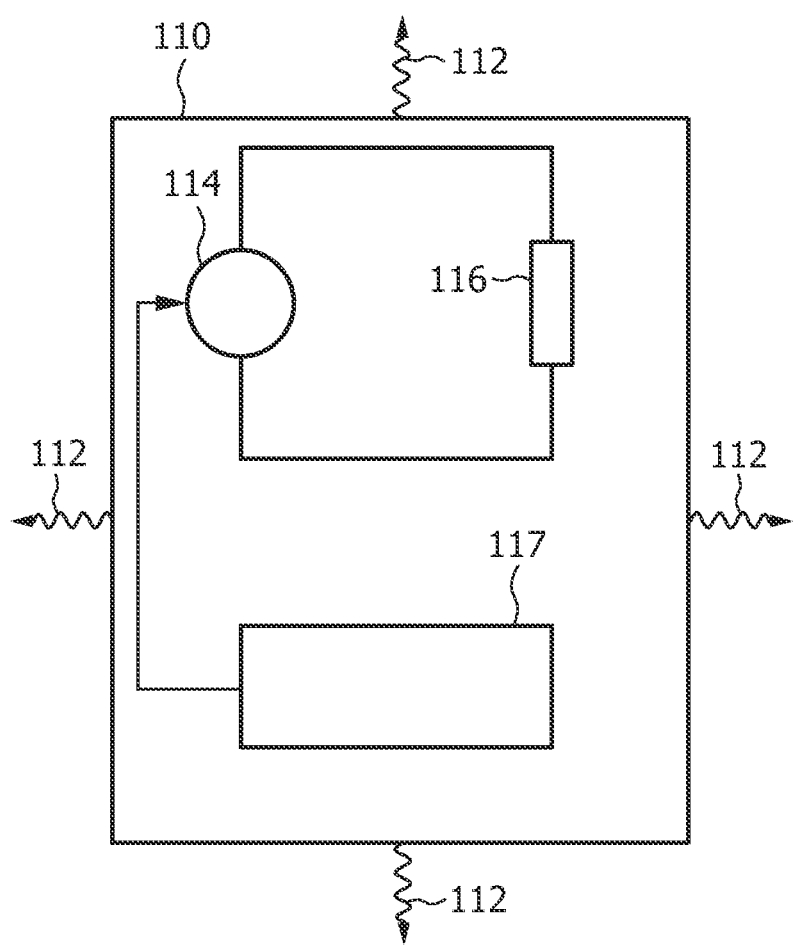
FIG. 2 shows schematically and exemplarily a representation of an embodiment of the heater of the contact detection device in accordance with the first aspect of the invention.

FIG. 2 shows schematically and exemplarily a representation of an embodiment of the heater 110 of the contact detection device 100 in accordance with the first aspect of the invention. In this embodiment, the heater 110 is realized by a power source 114 and a thermal resistor 116. Within the scope of this description, the wording "thermal resistor" refers to all classes of temperature dependent resistors exhibiting either a positive or negative temperature coefficient, such as a thermistor or a resistance thermometer.

In a preferred embodiment, the thermal resistor 116 connected to the power source 114 is a thermistor 116. This has the advantage of a very small size and low cost. For example, the thermistor 116 can have an approximate size of $(0.5\,\text{mm})^3$ with negligible costs. Therefore, the contact detection device 100 may be advantageously integrated in other devices. The thermistor 116 may exhibit either a positive or negative temperature coefficient. The thermistor 116 is commonly composed of a ceramic or polymer. A resistance thermometer is commonly composed of a substantially pure metal. Preferentially, the thermal resistor 116 is connected to the temperature sensitive contact surface 111 of the contact detection device 100.

Preferentially, the power source 114 is a current source or a voltage source providing a modulated current or a modulated voltage, respectively, to the thermal resistor 116. The power dissipation of the thermal resistor 116 represents the modulated heat flow 112. That modulated heat flow 112 is directly proportional to the resistance of the thermal resistor 116. The resistance of the thermal resistor 116 is further a function of the temperature of the thermal resistor 116. The thermal resistor 116 may exhibit either a positive or negative temperature coefficient. If the contact detection device 100 contacts an object 800, the temperature difference effects a heat exchange between the object 800 and the contact detection device 100 which causes an increase or decrease of the resistance value of the thermal resistor 116 and therefore a decrease or an increase in voltage or current, respectively, and ultimately a change in the generated heat flow.

It is emphasized that a difference in temperature is not an absolute requirement for the detection of the presence of a physical contact. A deviation in the modulated heat signal 122 may also result from a change in the total heat capacity caused by the physical contact to the object. That change in the total heat capacity implies a deviation in the modulated heat flow 112 that effects the modulated heat signal 122.

In a preferred embodiment, the power source 114 is a current source that provides a modulated current. The modulated heat signal 122 is preferentially a measured voltage of the thermal resistor 116 and the heat signal generation unit 120 consequently a voltmeter.

In an alternative preferred embodiment, the power source 114 is a voltage source that provides a modulated voltage. The modulated heat signal 122 is preferentially a measured current of the thermal resistor 116 and the heat signal generation unit 120 consequently a current meter. In this embodiment, the heat signal generation unit 120 can also be a voltmeter. In this case, an additional resistance of substantially constant resistance is preferentially connected in series to the thermal resistor 116.

Depending on the shape of the desired modulated heat flow 112, either a current or a voltage source may be advantageous.

In a further preferred embodiment, the power source 114 is controlled by a controller 117 of the contact detection device 100 such that the modulated heat flow 112 provided by the controlled heater 110 seeks to effect a predefined course of temperature of the thermal resistor 116. For example, the controller 117 is a proportional-integral controller 117. The power source 114 is then realized, for instance, by a proportional-integral controlled current or voltage source. The controller 117 can be integrated in the heater. Alternatively, the controller 117 can be arranged externally from the heater.

In this embodiment, the heat signal generation unit 120 is preferentially a power consumption measurement unit and adapted to generate a power consumption value of the heater 110 as the modulated heat signal 122. When contacting an object 800, the temperature of the thermal resistor 116 deviates. As the controller 117 controls the heater 110, power consumption of the heater 110 deviates contrary to the deviation of the temperature of said temperature sensitive part, such the deviation in temperature is reduced. A measured power consumption value is therefore a suitable modulated heat signal 122 to derive the contact indication signal 132 from.

Figure 3:
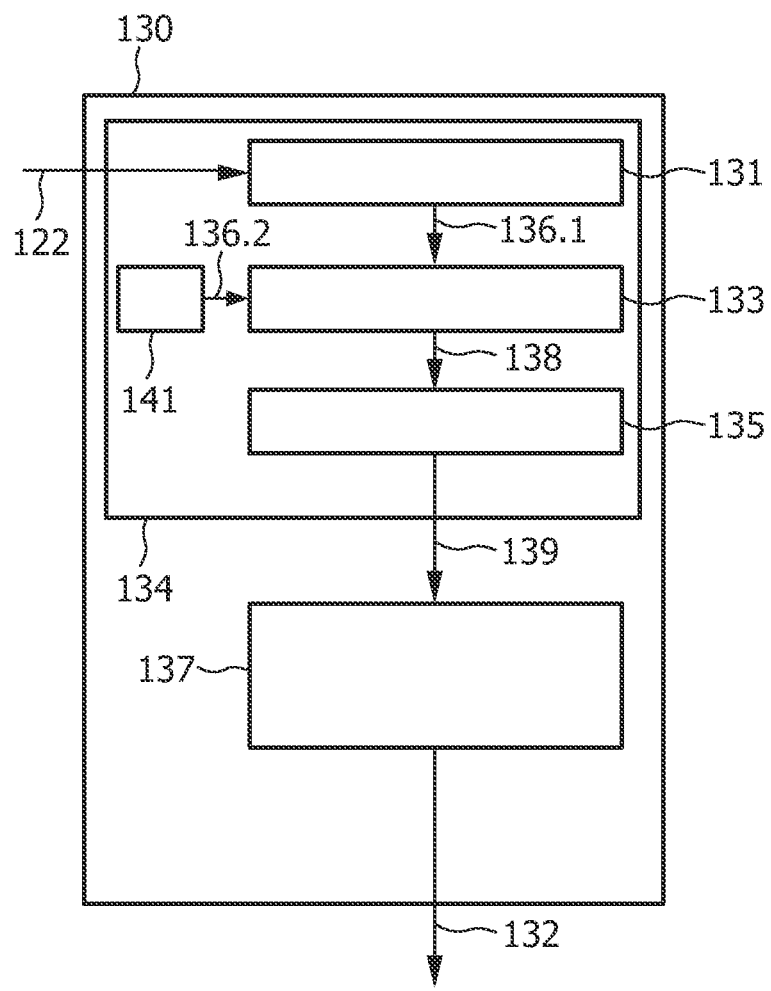
FIG. 3 shows schematically and exemplarily a representation of an embodiment of the contact determination unit of the contact detection device in accordance with the first aspect of the invention.

FIG. 3 shows schematically and exemplarily a representation of a preferred embodiment of the contact determination unit 130 of the contact detection device 100 in accordance with the first aspect of the invention. The determination unit comprises a demodulator 134 for demodulating the modulated heat signal 122 to generate a demodulated signal 139 and is adapted to determine the contact indication signal 132 depending on the demodulated signal 139.

This preferred embodiment of the contact detection device 100 of the first aspect of the invention has the advantage that an influence of the ambient temperature is reduced and the reliability of the contact detection device 100 furthermore improved. The generated demodulated signal 139 contains regained information carrying parameters characterizing the modulated heat flow 112, such as the amplitude, phase or duty cycle of the modulated heat flow 112 or the frequency of periodic modulated heat flow 112. As for instance the frequency of the periodic modulated heat flow 112 differs significantly from a rate of change in the ambient temperature, the demodulated signal 139 is substantially independent from the ambient temperature. Therefore, the contact determination unit 130 derives the contact indication signal 132 only from a signal, which depends nearly exclusively on the modulated heat flow 112 and not on the ambient temperature. Therefore, the reliability of the contact detection device 100 is again increased.

In this preferred embodiment the demodulator 134 comprises a first calculation unit 131 being adapted to determine a constant component of the modulated heat signal 122 and to subtract the constant component of the modulated heat signal 122 from the modulated heat signal 122 to generate a first alternating signal 136.1. Preferentially, that constant component is a time averaged component.

The modulated heat flow $HF_{DC}(t)$ (112) provided by the heater 110 can for instance be expressed according to equation (1)

$$HF_{DC}(t)=HF_0+A_1\cdot\sin(\omega t)+(t), \tag{1}$$

where $HF_0$ is a substantially non-alternating component of the modulated heat flow 112, $A_1\cdot\sin(\omega t)$ an alternating component, wherein $A_1$ characterizes the amplitude of the alternating component, $\omega$ the frequency of the alternating component and $t$ the time. $E_1(t)$ characterizes an error term caused by common side effects. For example, if the modulated heat flow 112 is provided by generating a sinusoidal current, this error term is proportional to a squared sine wave.

However, the modulated heat flow 112 provided by the heater 110 can be of any other shape than of a sinusoidal shape, for example a shape of a periodic rectangular signal, of a sawtooth signal, of a pulse width modulated signal or of a pseudorandom signal. In particular, the shape of the modulated heat flow 112 provided by the heater 110 can assume a squared characteristic of the aforementioned shapes.

According to the modulated heat flow 112 of equation (1), the heat signal generation unit 120 generates a modulated heat signal $HS_{DC}(t)$ (122) according to equation (2)

$$HS_{DC}(t)=HS_0(T_{amb},T_{obj})+A_2(C_{obj})\cdot\sin(\omega\cdot t)+E_2(t), \tag{2}$$

where $HS_0$ is a component substantially depending on the ambient temperature $T_{amb}$. If the contact detection device 100 is in physical contact with an object 800, this component also depends on a temperature $T_{obj}$ of the object 800. An alternating component of the modulated heat signal 122 is characterized by the term $A_2(C_{obj})\cdot\sin(\omega\cdot t)$. The amplitude $A_2$ of the alternating component depend on the location of the object 800, whether or not it is in contact with the contact detection device 100. A physical contact changes the total heat capacity that is fed by the heater 110. The total heat capacity fed by the heater 110 depends on the heat capacity $C_{obj}$ of the object 800, if the object 800 is in contact with the contact detection device 100. That heat capacity $C_{obj}$ of the object 800 also depends on the temperature $T_{obj}$ of the object 800. As the heat signal generation unit 120 generates the modulated heat signal 122 in dependence of the modulated heat flow 112, an error term $E_2(t)$ remains part of the modulated heat signal 122.

The first calculation unit 131 of the demodulator 134 of the contact determination unit 130 is adapted to determine the constant component $HS_{CONST}$ of the modulated heat signal 122 and to subtract the constant component $HS_{CONST}$ from the modulated heat signal $HS_{DC}(t)$ (122) to generate the first alternating signal $HS_{AC}$ (136.1) according to equation (3)

$$HS_{AC}=HS_{DC}-HS_{CONST} \tag{3}$$

The first alternating signal $HS_{AC}$ (136.1) is therefore substantially independent from the ambient temperature.

The demodulator 134 further comprises a multiplier 133. The multiplier 133 of the demodulator 134 of the contact determination unit 130 is adapted to multiply the first alternating signal $HS_{AC}$ (136.1) with a second alternating signal 136.2 to generate the intermediate signal $HS_{INTER}$ (138), the second alternating signal 136.2 being in phase with the modulated heat flow 112; for example according to equation (4)

$$HS_{INTER}=HS_{AC}\cdot\sin(\omega t) \tag{4}$$

Preferentially, the contact determination unit 130 is adapted to determine the second alternating signal 136.2 by detecting a phase of the modulated heat flow 112, for example by means of detecting signals in noise, such as in-phase or quadrature synchronous detection, matched filter, frequency domain analysis like Fast Fourier Transformation or Discrete Cosine Transformation or single tone extraction. Alternatively, the second alternating signal 136.2 can be provided by the phase detection unit 141 of the contact detection device 100.

Ultimately, the demodulator 134 further comprises an average calculation unit 135. The average calculation unit 135 is adapted to average the intermediate signal $HS_{INTER}$ (138) to generate the demodulated signal $HS_{DEMOD}$ (139), preferentially by low-pass filtering the intermediate signal $HS_{INTER}$ (138) according to equation (5)

$$HS_{DEMOD}=LPF(HS_{INTER}), \tag{5}$$

where LPF is a low-pass filtering function. In a preferred embodiment, the average calculation unit 135 is moving average filter. In a further preferred embodiment, the average calculation unit 135 is a butterworth filter. Preferentially the cut-off frequency of both filters is lower than the frequency of the modulated heat flow 112, for instance its value is approximately equal to the half of the value of the frequency of the periodic modulated heat flow 112. The generated demodulated signal $HS_{DEMOD}$ (139) is well suitable for determining the contact indication signal 132, as its value significantly changes if a physical contact between the contact detection device 100 and an object 800 is made.

Preferentially, the contact determination unit 130 further comprises a comparator 137 for comparing the demodulated signal 139 with a threshold and is adapted to determine the contact indication signal 132 depending on a result of the comparison. Preferentially, the contact indication signal 132 indicates the presence of the physical contact if a value of the demodulated signal 139 is below the threshold and indicates the absence of the physical contact if a value of the demodulated signal 139 above the threshold. Alternatively it is preferred that the contact indication signal 132 indicates the absence of the physical contact if a value of the demodulated signal 139 is below the threshold and indicates the presence of the physical contact if a value of the demodulated signal 139 above the threshold. Depending on the nature of the modulated heat signal 122 and the definition of the threshold, the first or the second of the above mentioned two possibilities is advantageous.

In this embodiment, the contact determination unit 130 can be adapted such that if the demodulated signal 139 is equal to the threshold, the contact indication signal 132 either indicates presence of the physical contact or absence of the physical contact.

The threshold can be a constant predefined threshold or a changing threshold. Preferentially, the threshold is defined in dependence of the generated modulated heat flow 112 and/or in dependence of a demodulation function of the demodulator 134 of the contact determination unit 130. This has the advantage that sudden changes of the modulated heat signal 122 can be detected by the contact determination unit 130. Therefore, the reliability of the contact detection device 100 is furthermore improved.

Figure 4:
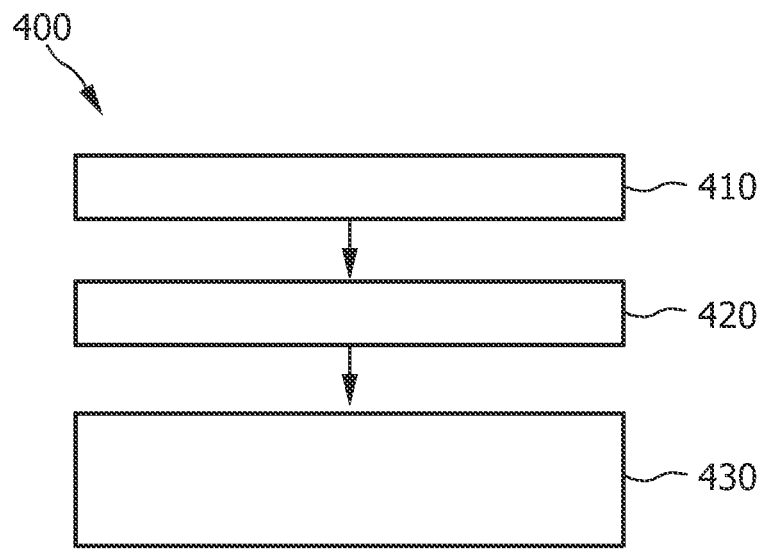
FIG. 4 shows exemplarily a flowchart illustrating an embodiment of the method of operating a contact detection device for detecting a physical contact between the contact detection device and an object in accordance with the second aspect of the invention and FIG. 5 shows schematically and exemplarily a representation of the diagnostic device in accordance with the third aspect of the invention.

The contact detection device 100 for detecting a physical contact between the contact detection device 100 and an object 800 of the first aspect of the invention may be operated according to the method 400 illustrated in FIG. 4. In a first step 410, a modulated heat flow 112 is provided. This may be done by using a thermal resistor 116 connected to power source 114, wherein the power source 114 provides a modulated current or a modulated voltage. Preferentially a periodic modulated heat flow 112 is provided, wherein the rate of change of the modulated heat flow 112 is preferentially greater than a common rate of change of an ambient temperature.

The provided modulated heat flow 112 can be of any shape, for example a shape of a periodic rectangular signal, of a sinusoidal wave, of a sawtooth signal, of a pulse width modulated signal or of a pseudorandom signal. In particular, the shape of the modulated heat flow 112 provided by the heater 110 can assume a squared characteristic of the aforementioned shapes.

Due to the modulated heat flow 112, at least a temperature sensitive contact surface 111 of the contact detection device 100 assumes a modulated temperature $T_{mod}$. When contacting an object 800 exhibiting a temperature $T_{obj}$, the difference in temperature $\Delta T=|T_{obj}-T_{mod}|$ causes a change in the amount of the modulated heat flow 112, since either heat flows from the contact detection device 100 to the object 800 or from the object 800 to the contact detection device 100. That difference in temperature comprises an alternating and a substantially non-alternating component. The alternating component is caused by the modulated heat flow 112, the substantially non-alternating component characterizes a time averaged temperature difference. As it is most unlikely that the temperature of the object 800 changes in the same manner as the modulated heat flow 112, a change in heat flow is quasi assured if contact is made with the object 800.

In a second step 420, a modulated heat signal 122 is generated in dependence of the modulated heat flow 112. This may be done by using a thermometer and generating a temperature signal as a modulated heat signal 122. A change in the amount of the modulated heat flow 112 therefore effects a change in the modulated heat signal 122.

In a third step 430, a contact indication signal 132 indicating at least either the presence or the absence of the physical contact is determined depending on the modulated heat signal 122. Preferentially, this step is carried out by detecting a deviation in the modulated heat signal 122.

Since it is most unlikely that the temperature of an object 800 changes in the same manner as the modulated heat flow 112, that deviation in the modulated heat signal 122 is quasi assured.

The provided modulated heat flow 112 that effects the modulated heat signal 122 not only changes if the temperature of the temperature sensitive contact surface 111 of the contact detection device 100 differs from the temperature $T_{obj}$ of the object 800: The invention is based on the further recognition that the total heat capacity, which is fed by the modulated heat flow 112, changes as well, if the contact detection device 100 physically contacts the object 800. Therefore, parameters that define the shape of the modulated heat flow 112, such as a frequency of the modulated heat flow 112 and/or a rate of change of the modulated heat flow 112 and/or an amplitude of the modulated heat flow 112, change as well.

Therefore, a change of the modulated heat signal 122 that is generated in dependence of the modulated heat flow 112 is quasi assured, if a physical contact between an object 800 and the contact detection device 100 is made. Therefore a detection of the presence or the absence of the physical contact between the contact detection device 100 and the object 800 is quasi assured.

Figure 5:
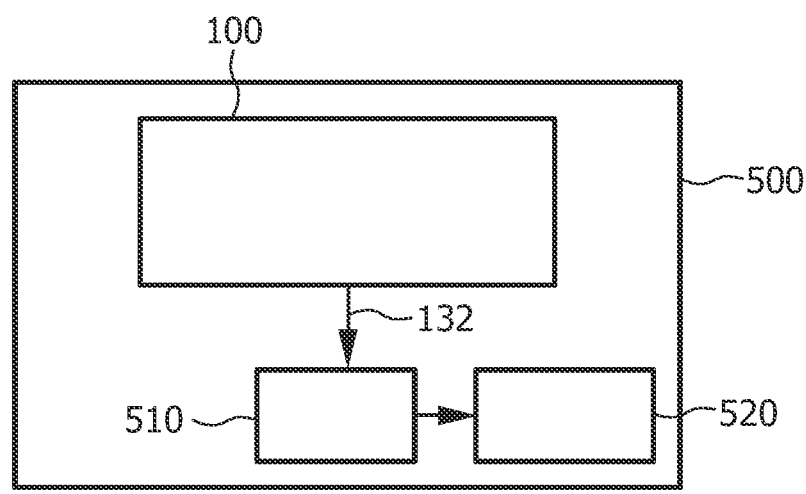

FIG. 5 shows schematically and exemplarily a representation of the diagnostic device 500 in accordance with the third aspect of the invention. The diagnostic device comprises a contact detection device 100 of the first aspect of the invention.

This has the advantage that a diagnosis of an object is can be performed after a physical contact between the diagnostic device 500 and the object is ascertained by the contact detection device of the diagnostic device. This advantage is of particular significance in the field of clinical application.

In one embodiment, the diagnostic device 500 of the third aspect of the invention can be a medical device, such as a temperature sensor, in particular a human body sensor. Some temperature sensors only function if they are properly attached to the object whose temperature is to be measured. Therefore, it is advantageous if such a temperature sensor comprises a contact detection device 100 indicating the presence or the absence of a physical contact.

In another embodiment, the diagnostic device 500 is an occupancy detection device for detecting the occupancy of an apparatus, such as a bed or chair.

In a preferred embodiment of the diagnostic device 500, the contact indication signal 132 provided by the contact detection device 100 is used for operating a switch 510 of the diagnostic device 500. The switch 510 of the diagnostic device 500 is preferentially employed for activating or deactivating, respectively, further processing means 520 of the diagnostic device.

In the above described embodiments, certain equations are used for generating a demodulated signal. The contact indication signal is determined in dependence of the demodulated signal. In other embodiments, other equations can be used for generating the demodulated signal.

Also in the above described embodiment, certain processing means of the contact determination unit are adapted to carry out the above described equations. In other embodiments, these processing means are adapted to carry out further equations to generate the demodulated signal. In particular, the contact determination unit can comprise an alternative arrangement and/or an alternative set of processing means for determining the contact indication signal as described in the above mentioned embodiments.

In the above described embodiment, the contact indication signal indicates at least either the presence or the absence of a physical contact. In other embodiments, the contact indication signal serves further purposes, such as operating a switch.

Other variations to the disclosed embodiments can be understood and effected by those skilled in the art in practicing the claimed invention, from a study of the drawings, the disclosure, and the appended claims.

It shall be understood that an arrangement of elements of a respective figure predominately serves a purpose of an evident description; it does not relate to any actual geometric arrangement of parts of a manufactured device according to the invention.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The present invention is related to a contact detection device for detecting a physical contact between the contact detection device and an object, a method of operating a contact detection device, a diagnostic device comprising a contact detection device and further to a computer program. The invention seeks to improve the reliability of contact sensors. The contact detection device comprises a heater for providing a modulated heat flow. A modulated heat signal is generated in dependence of the modulated heat flow. A physical contact with an object causes a change in the modulated heat flow that effects the modulated heat signal. As the heat flow is modulated, a change in the modulated heat signal is quasi assured. A contact determination unit of the contact detection device derives a contact indication signal indicating at least either the presence or the absence of the physical contact from the modulated heat signal, preferentially by means of a demodulator.

The invention claimed is:

1. A contact detection device for detecting a physical contact between the contact detection device and an object based on a change in heat capacity, the contact detection device comprising:
   a heater which heats a temperature sensitive contact surface;
   a power source which provides at least one of a modulated voltage, a modulated current, and a modulated power to the heater such that the heater generates a modulated heat flow to the temperature sensitive contact surface,
   a heat signal generation unit which generates a modulated heat signal indicative of the modulated heat flow based on the modulated voltage, the modulated current, or the modulated power,
   a contact determination unit which generates a contact indication signal indicating at least either the presence or the absence of the physical contact depending on the generated modulated heat signal.

2. The contact detection device of claim 1, wherein the heater includes a thermal resistor connected to the power source.

3. A diagnostic device comprising:
   a processor;
   a switch which enables the processor; and
   the contact detection device of claim 1 which controls the switch in accordance with the contact indication signal.

4. The contact detection device of claim 1, wherein the modulated heat signal includes a DC component and an AC component, and wherein the contact determination unit generates the contact indication signal based on an amplitude of the AC component.

5. The contact detection device of claim 4, wherein the contact determination unit includes a demodulator for demodulating the AC component of the modulated heat signal to generate a demodulated signal and generating the contact indication signal based on the demodulated signal.

6. The contact detection device of claim 5, wherein the demodulator is configured to demodulate the AC component of the modulated heat signal in phase with the modulated heat flow.

7. A contact detection device for detecting a physical contact between the contact detection device and an object, the contact detection device comprising:
   a heater for providing a modulated heat flow;
   a heat signal generation unit configured to generate a modulated heat signal indicative of the modulated heat flow;
   a contact determination unit for generating a contact indication signal indicating at least either the presence or the absence of the physical contact depending on a demodulated signal, the contact determination unit including a demodulator which includes:
      a first calculation unit configured to determine a constant component of the modulated heat signal and to subtract the constant component of the modulated heat signal from the modulated heat signal to generate a first alternating signal,
      a multiplier configured to multiply the first alternating signal with a second alternating signal to generate an intermediate signal, wherein the second alternating signal is in phase with the modulated heat flow,
      an average calculation unit for averaging the intermediate signal to generate the demodulated signal.

8. The contact detection device of claim 7, wherein the contact determination unit comprises a comparator for comparing the demodulated signal with a threshold and is adapted to determine the contact indication signal depending on a result of the comparison.

9. The contact detection device of claim 7, additionally comprising a controller for controlling the heater such that the modulated heat flow provided by the controlled heater seeks to effect a predefined course of temperature of the heater.

10. The contact detection device of claim 7, wherein the heater is configured to provide a constant heat flow.

11. A diagnostic device comprising:
    a processor;
    a switch which enables and disables the processor; and
    the contact detection device of claim 7 which controls the switch in accordance with the contact indication signal.

12. A method of operating a contact detection device for detecting a physical contact between the contact detection device and an object based on a change in heat capacity of a temperature sensitive contact surface of the contact detection device due to contact with the object, the method comprising following steps:
    providing a modulated heat flow to the temperature sensitive contact surface,
    generating a modulated heat signal in dependence of the modulated heat flow,
    demodulating modulated heat signal,
    determining a contact indication signal indicating at least either the presence or the absence of the physical contact depending on the demodulated signal.

13. A non-transitory computer-readable medium carrying a computer program for controlling a contact detection device to carry out the steps of the method as defined in claim 12, when the computer program is run on a computer controlling the contact detection device.

14. The method of claim 12, wherein the modulated heat signal includes a DC component indicative primarily of ambient temperature of the temperature sensitive contact surface and an AC component indicative primarily of the modulated heat flow to the temperature sensitive contact surface and wherein only the AC component is demodulated such that the contact indication signal is substantially independent of the ambient temperature.

* * * * *